United States Patent
Maitre (10) Patent No.: US 8,758,782 B2
(45) Date of Patent: Jun. 24, 2014

(54) EXCIPIENT PRESERVATIVES AND PHARMACEUTICAL COMPOSITIONS COMPRISED THEREOF

(75) Inventor: Lydie Maitre, Nice (FR)

(73) Assignee: Galderma Research & Development, Biot (FR)

( * ) Notice: Subject to any disclaimer, the term of this patent is extended or adjusted under 35 U.S.C. 154(b) by 841 days.

(21) Appl. No.: 12/720,802

(22) Filed: Mar. 10, 2010

(65) Prior Publication Data

US 2010/0222333 A1 Sep. 2, 2010

Related U.S. Application Data (63) Continuation of application No. PCT/FR2008/051648, filed on Sep. 12, 2008.

(60) Provisional application No. 60/960,043, filed on Sep. 12, 2007.

(51) Int. Cl.
*A61K 8/18* (2006.01)

(52) U.S. Cl.
USPC .......................................... 424/401

(58) Field of Classification Search
None
See application file for complete search history.

(56) References Cited

U.S. PATENT DOCUMENTS

| 4,213,979 | A | * | 7/1980 | Levine | 514/171 |
| 5,002,938 | A | * | 3/1991 | Wang et al. | 514/171 |
| 2003/0054020 | A1 | * | 3/2003 | Niazi | 424/401 |
| 2003/0199477 | A1 | | 10/2003 | Fanara et al. | |

FOREIGN PATENT DOCUMENTS

| EP | 1803464 A1 | 7/2007 |
| EP | 1813263 A1 | 8/2007 |
| WO | WO 2006/075123 A1 | 7/2006 |
| WO | WO2006075123 A * | 7/2006 |
| WO | WO20060175123 A * | 7/2006 |

OTHER PUBLICATIONS

Jurkovic et al. (Skin Protection against Ultraviolet induced free radicals with ascrobyl palmitate in microemulsions, available Jul. 2003).*
International Search Report corresponding to PCT/FR 2008/051648 issued May 13, 2009.

* cited by examiner

*Primary Examiner* — Anand Desai
*Assistant Examiner* — Melissa Mercier
(74) *Attorney, Agent, or Firm* — Dentons US LLP (57) ABSTRACT

Topically applicable pharmaceutical compositions contain at least one pharmaceutically active agent and an effective antimicrobial amount of a preservative excipient mixture and devoid of such amount of known preservative(s) as would otherwise itself impart an effective antimicrobial action thereto.

20 Claims, 4 Drawing Sheets

EXCIPIENT PRESERVATIVES AND PHARMACEUTICAL COMPOSITIONS COMPRISED THEREOF

CROSS-REFERENCE TO EARLIER APPLICATIONS

This application is a continuation of PCT/FR2008/051648, filed Sep. 12, 2008 and designating the United States (published in the French language on Apr. 16, 2009 as WO 2009/047434 A2; the title and abstract were also published in English), which claims priority under 35 U.S.C. §120 of U.S. Provisional Application No. 60/960,043, filed Sep. 12, 2007, each hereby expressly incorporated by reference in its entirety and each assigned to the assignee hereof.

BACKGROUND OF THE INVENTION

1. Technical Field of the Invention

The present invention relates to the formulation of a combination of excipients into pharmaceutical compositions because of their preservative activity, and to the topically applicable pharmaceutical compositions comprising same. The present invention therefore also relates to the combination of excipients having a good preservative activity.

2. Description of Background and/or Related and/or Prior Art

A topical pharmaceutical or cosmetic composition is often a good substrate for the proliferation of microorganisms.

Two major families of microorganisms exist, bacteria and fungi. The European and U.S. pharmacopoeias, that those skilled in the art in the more particular field of pharmaceutical products are duty-bound to follow, have selected, in total, five microorganisms representative of these families, three species of bacteria and two types of fungi.

The following three species of bacteria are representative of the microbial population commonly encountered in contaminations and are capable of causing an infection in humans. *Escherichia coli* is a gram-negative bacterium. It has a thin wall which is permeable to small molecules. It has a rod shape, known as bacillus. This bacterium is present essentially in fecal waste. Its presence can cause various diseases, such as gastroenteritis. *Staphylococcus aureus* is a gram-positive bacterium. It therefore has a thicker wall which is impermeable to small molecules. It is spherical in shape and is referred to as a coccus, as its name indicates. *Staphylococcus aureus* is the most pathogenic species of the *Staphylococcus* genus. It is responsible for food poisoning and for suppurative localized infections. *Pseudomonas aeruginosa* is a gram-negative bacterium of the *Pseudomonas* genus. The bacilli are thin, straight and very mobile owing to a polar flagellum. It is pathogenic and commonly encountered in nosocomial infections.

Fungi are eukaryotes with a nucleus surrounded by a membrane and containing the chromosomes. Two types thereof exist, yeast and moulds. *Candida albicans* is the most important and most well-known yeast species of the *Candida* genus. It is an organism which lives naturally in the mouth and the digestive tract of human beings. It is found in 80% of the population, and it does not usually lead to any particular disease or symptom. It is a saprophytic commensal organism which becomes pathogenic if the carrier organism becomes weakened. The mould studied is *Aspergillus niger*. It is very widespread (fruit and vegetables that have gone moldy, fodder, dairy products). It is widely used in the food-processing industry for the production of various acids. This species can be pathogenic (aspergillosis of the auditory canal, production of ochratoxin).

There are a very large number of possible sources of microbial contaminations of topical products. The microorganisms originate mainly from humans or from the environment, and intervene at various times of the processing, storage or use of the product.

Those formulating pharmaceutical compositions must therefore integrate this problem very early into the development of a topical composition. The addition of a preservative is often the solution adopted.

An antimicrobial preservative is a substance or a set of substances which is added intentionally to a formulation in order to prevent the proliferation of microorganisms. These preservatives should be introduced in a small amount, have a broad spectrum of action and be devoid of toxicity, and should not offset the efficacy of the active ingredients used.

A preservative agent does not always have a spectrum of activity that is broad enough to inhibit all the microorganisms indicated above. For this reason, combining said preservative agents according to their activity is a commonly used approach. By combining them correctly, the preservative system obtained acts on all the microorganisms.

A large variety of antimicrobial preservative agents that can be used in topical products exists. However, while this list is long for products for cosmetic applications, it is restricted for pharmaceutical products. In fact, only about ten preservatives are normally employed in this environment.

This difference comes from the fact that, during the clinical study, the pharmaceutical products must be completely tolerated by or completely innocuous to humans.

The preservatives normally employed in the pharmaceutical field are, for example, formaldehyde-generating agents, such as imidazolidinylurea or diazolidinylurea, thiazins derivatives, such as Kathon™ CG (methylchloroisothiazolinone (MCI)), chlorinated derivatives, such as chlorhexidine, phenolic derivatives, such as parabens, alcoholic derivatives, such as bronopol, phenoxyethanol or chloroxylenol, acid derivatives, such as sorbic acid or benzoic acid, or benzaikonium chloride.

The preservatives which are preferred and more conventionally included in pharmaceutical compositions are parabens, in particular methylparaben, propylparaben, ethylparaben or butylparaben, and phenoxyethanol, alone or as mixtures.

The most common preservative agents are parabens, ideally combined with phenoxyethanol.

However, phenoxyethanol can become a substance that is toxic to the user at high doses. For healthy individuals, the concentrations necessary for toxicity are high. However, phenoxyethanol is a recognized allergen. The use thereof can cause eczema plaques in certain individuals.

Moreover, the parabens themselves also exhibit toxicity at high doses.

In general, those skilled in the art are aware that the preservatives normally employed in topical formulations can be potentially sensitizing, irritant and/or allergenic. For all these reasons, it becomes important to limit their use or even to completely remove them from the formulations. However, if a preservative system is not added, the antimicrobial protection will not be effective. For this reason, it is important to determine another approach that can provide this function.

Certain factors, such as the temperature of the medium, the pH or the water content, influence the colonization by microorganisms, and those skilled in the art have studied the possibility of modifying these factors. The temperature of the medium does not have a really bactericidal or fungicidal effect. Bacteria develop at around 32.5° C. and fungi around 22.5° C. If a formulation is stored above or below these temperatures, for example in a refrigerator at +4° C., the microorganisms will become dormant and will not develop. If the temperature becomes favorable again, the microorganisms will once again be able to grow. Maintaining at high temperature (>+75° C.) or low temperature (<+4° C.) presents numerous constraints, whether during production or during use.

If the pH of the composition is very acidic or very basic, microorganism development will be limited. However, moulds are tolerant to a very broad pH range, and thus the development thereof will nevertheless be possible. The use of a topical composition at high or low pH also has its limits. This is because the application of a very acidic or basic solution or cream to the skin can have irritant effects.

The water content is also a very important point. This is because the presence of water is essential for the proliferation of microorganisms. Thus, if the medium is completely anhydrous, their proliferation will be inhibited. However, those skilled in the art in the pharmaceutical and cosmetic sector cannot envisage only anhydrous compositions, which are very often not as pleasant as emulsion or gel compositions. Moreover, many pharmaceutical active ingredients are water-soluble and therefore require the presence of water in the compositions. Without having to eliminate the water, those skilled in the art must take into account the water activity in the composition. The water activity is not exactly the amount of water, but the amount of free water in a medium. The free water is the water which does not serve to solvate the molecules introduced into the aqueous medium.

This free water is therefore completely accessible to the microorganisms in order to provide proliferation thereof.

The water activity (aw) is an intrinsic value of the medium studied, it does not depend on any external parameter. The aw ranges from 1.00 for pure water to 0.00 for a completely anhydrous medium.

The water requirements of each of the microorganisms is different. Bacteria, for example, are more sensitive to the presence of water than moulds.

Table 1 below is the water activity required for various microorganisms in order for them to develop.

TABLE 1

Values of water activity necessary for microorganism growth:

| Microorganism | Water activity |
|---|---|
| Average for bacteria | 0.91 |
| Pseudomonas aeruginosa | 0.97 |
| Escherichia coli | 0.95 |
| Staphylococcus aureus | 0.86 |
| Average for yeast | 0.86 |
| Candida albicans | 0.88 |
| Average for moulds | 0.80 |
| Aspergillus niger | 0.77 |

Thus, if the aw is less than 0.77, the microorganisms set forth in this table will not be able to develop.

It therefore becomes important to be aware of the means which induce a reduction in water activity.

The first, and the most obvious, is to reduce the amount of water introduced into the formulations.

The second comprises determining molecules that would have a considerable solvating capacity. Thus, the water would be mobilized to a greater extent in order to solvate these molecules and would be less available for the microorganisms. Humectants, mineral salts and hydrocolloids may play this role.

The measurement of the water activity of formulations has very recently been the subject of a chapter of the general methods of the U.S. pharmacopoeia ("Application of water activity determination to nonsterile pharmaceutical products <1112> USPC Official May 1, 2007-Jul. 31, 2007, 2007").

The literature describes self-preservative compositions and lists excipients that are known to have a preservative activity. Thus, Jon J. Kabara (and D. S. Orth in "*Preservative-free and self-preservative Cosmetics and Drugs—Principles and Practice*", published by Dekker, New York, 1996) lists various categories of excipients capable of having a preservative activity in the composition, such as alcohol, surfactants, fatty esters or acids, phospholipids, antioxidants or chelating agents. However, a large number of these ingredients taken alone or as a mixture fail to meet the criteria required by the pharmacopoeias, or meet them at concentrations that are not acceptable in a pharmaceutical composition. They cannot therefore be used as such and readily by those skilled in the art faced with the regulatory requirements, in pharmaceutical compositions.

The most active surfactants are cationic surfactants. However, the latter can essentially be included in compositions in the form of shampoos, a pharmaceutical form that is not a major one in the sector. In fact, those skilled in the art more particularly formulate emulsions or gels.

Moreover, J. J. Kabara has described that the proliferation of microorganisms can be prevented with ethanol, but starting from 25% (v/v). However, on the one hand, these percentages are extremely high for good tolerance of a topical pharmaceutical composition, and, on the other hand, nothing in the literature confirms the reductions actually observed for each microorganism, as must be the case in accordance with the pharmacopoeias.

The problem addressed by the present invention is therefore that of finding an alternative to the conventional preservatives in order to effectively protect a pharmaceutical, topical composition against the microorganisms indicated above.

The term "known preservatives" means, for example, formaldehyde-generating agents, such as imidazolidinylurea or diazolidinylurea, thiazins derivatives, such as Kathon™ CG (methylchloroisothiazolinone (MCI)), chlorinated derivatives, such as chlorhexidine, phenolic derivatives, such as parabens, alcoholic derivatives, such as bronopol, phenoxyethanol or chloroxylenol, acid derivatives, such as sorbic acid or benzoic acid, or benzalkonium chloride.

The preservatives most commonly formulated into compositions, in particular by the assignee hereof, are parabens, in particular methylparaben, propylparaben, ethylparaben or butylparaben, and phenoxyethanol, alone or as mixtures.

The problem addressed by the invention is therefore that of limiting, or even eliminating, the preservatives in a pharmaceutical topical composition.

A particular problem that must be solved by the invention is that of effectively protecting a pharmaceutical topical composition while at the same time meeting the criteria required by the European and U.S. pharmacopoeias. This is because, since the purpose of the pharmaceutical composition is to become a pharmaceutical product with a marketing authorization, it is imperative for the composition according to the invention to meet these criteria. In order to verify this point and to determine the antimicrobial action of the various mixtures of excipients according to the invention, a test protocol, known as the PET (Preservative Efficacy Test), exists. The PET comprises artificially inoculating the compositions with a known number of microorganisms, and then determining the decrease in the latter in the compositions tested, at given times. The protocol of this test is set up in order to abide by the recommendations of the European and U.S. pharmacopoeias. The test and also the recommendations of the European and U.S. pharmacopoeias are described in Example 1 to follow. The mixture of excipients as preservatives, described herein, should therefore meet the criteria of these pharmacopoeias in the PET.

SUMMARY OF THE INVENTION

The present invention thus features topical pharmaceutical compositions containing a mixture of excipients as preservatives, characterized in that the composition does not contain any other, or very little conventional preservative.

The term "topical pharmaceutical composition" means any composition that those skilled in the art can envisage and, in particular but not exclusively, compositions in liquid form, or in pasty form, and more particularly in the form of emulsions, creams, milks, ointments, impregnated pads, syndets, wipes, gels, sprays, foams, lotions, sticks, shampoos or washing bases.

Preferably, because the protection of compositions containing water is the most complex, the present invention features compositions containing at least one aqueous phase containing water, preferably either an emulsion or a lotion.

The pharmaceutical composition comprising the preservative excipient mixture according to the invention is useful for treating the skin and is therefore administered topically. The term "topically" means application to the skin or the mucous membranes.

The term "preservative excipient mixture" means an ingredient mixture conventionally employed as formulation base, into which the active agent(s) is (are) introduced. By way of indication of excipients, solvents, in particular of ethanolic type, such as ethanol, surfactants, humectants and glycols are exemplary.

As indicated above, those skilled in the art are aware that ethanol has a considerable antimicrobial and antifungal action starting from 25% in the composition. However, it is difficult to make this concentration compatible with good tolerance for topical application to the skin of a patient.

It has now surprisingly been discovered that, by combining ethanol with other excipient compounds, it is possible to obtain good antimicrobial protection while at the same time reducing the ethanol concentration in the composition.

DETAILED DESCRIPTION OF BEST MODE AND SPECIFIC/PREFERRED EMBODIMENTS OF THE INVENTION

The preferred excipients according to the invention to be combined with ethanol are in particular humectants, antioxidants, surfactants, chelating agents and/or thickeners.

The term "humectant" means the humectants commonly employed topically. The action thereof makes it possible to maintain the water content in the stratum corneum. The humectants that can be used according to the invention are in particular, but not exclusively, glycerol and derivatives thereof, and glycols such as propylene glycol and polyethylene glycol.

The preferred humectants according to the invention are propylene glycol, glycerine or glycerol, or polyethylene glycol.

The term "antioxidants" means, according to the invention, natural antioxidants such as ascorbic acid compounds, citric acid compounds, tartaric acid compounds, lactates or tocopherols, or synthetic antioxidants such as butylhydroxyanisole (BHA), butylhydroxytoluene (BHT), tertiary butylhydroquinone (TBHQ) or propyl gallate.

Exemplary surfactants that can be used according to the invention are anionic, cationic, amphoteric or nonionic surfactants. Cationic surfactants are preferred, and in particular quaternary ammoniums and aminimides.

Exemplary chelating agents that can be used according to the invention are weak or labile chelating agents and strong chelating agents such as EDTA.

"Thickeners that can be used according to the invention" means in particular acrylic acid compounds, such as Carhopols® (for instance Ultrez 10 NF), cellulosic derivatives, such as Natrosol™, and xanthan gum.

The present invention more particularly features topical pharmaceutical compositions comprising a mixture of excipients containing at least ethanol and humectants.

The preferred humectants according to the invention are, for example, propylene glycol, glycerol or polyethylene glycol, in particular PEG 400, used alone or as a mixture.

Preferably, the excipient mixture which has good antimicrobial activity comprises, within the pharmaceutical composition, at least:
  from 5% to 25% of ethanol,
  from 1% to 50% of a humectant, selected from propylene glycol, glycerine or glycerol, and polyethylene glycol, alone or as a mixture.

More preferably, the composition also comprises an antioxidant within the preservative excipient mixture.

Preferably, the antioxidant is ascorbyl palmitate at a concentration of at least 0.5%, preferably at a concentration of 1% by weight, relative to the total weight of the composition.

According to another embodiment of the invention, the composition also comprises a thickener within the preservative excipient mixture.

Preferably, the thickener is a cellulosic derivative, such as Natrosol™, present at a concentration of at least 0.5%, preferably at a concentration of 1.5% by weight, relative to the total weight of the composition.

The present invention also features pharmaceutical compositions comprising the mixture of excipients according to the invention.

In one preferred embodiment of the invention, the composition therefore comprises a mixture of excipients as preservative, comprising:
  an antioxidant,
  a humectant,
  an ethanol/aqueous phase ratio ranging from 10% to 15%.

In another embodiment, the composition according to the invention may also take into account the water activity within the composition.

In one preferred embodiment of the invention, the composition therefore comprises a mixture of excipients as preservative, comprising:

ascorbyl palmitate at 1% by mass,
propylene glycol at 5% by mass,
a percentage of water of less than 50% by mass,
an ethanol/aqueous phase ratio ranging from 10% to 15%.

The present invention thus also features topical pharmaceutical compositions comprising a mixture of excipients having a microbial activity, said composition having from 0 to 1.8% by mass of preservatives selected from formaldehyde-generating agents, such as imidazolidinylurea or diazolidinyiurea, thiazine derivatives, such as Kathon™ CG (methylchloroisothiazolinone (MCI)), chlorinated derivatives, such as chlorhex idine, phenolic derivatives, such as parabens, alcoholic derivatives, such as bronopol, phenoxyethanol or chloroxylenol, acid derivatives, such as sorbic acid or benzoic acid, and/or benzalkonium chloride.

Such a composition is preferably in the form of an emulsion.

Said mixture of excipients of the composition as defined above is a mixture of ethanol, of humectant(s), of antioxidant(s), of surfactant(s), of chelating agent(s) and/or of thickener(s).

Said mixture of excipients preferably comprises:
from 5% to 25% of ethanol,
from 1% to 50% of humectant(s) selected from propylene glycol, glycerine or glycerol, and/or polyethylene glycol.

Preferably, the humectant is propylene glycol.

Said mixture of excipients also comprises an antioxidant, which is preferably ascorbyl palmitate.

Said mixture of excipients may also comprise a thickener present at a concentration of at least 0.5% by mass. Said thickener is preferably a cellulosic derivative such as Natrosol™.

Said composition as defined above comprises an ethanol/aqueous phase ratio of from 10% to 15%.

Said mixture of excipients comprises more particularly:
ascorbyl palmitate at a concentration of from 0.5% to 1% by mass,
propylene glycol at 5% by mass,
a percentage of water of less than 50% by mass,
an ethanol/aqueous phase ratio ranging from 10% to 15%.

More particularly, said composition as defined above contains less than 0.8% of parabens, and preferably less than 0.4% of propylparaben.

The pharmaceutical compositions according to the invention can be formulated as medicaments.

The present invention also features the formulation of the subject compositions into medicaments useful for treating dermatological conditions, in particular for treating human dermatological conditions and disorders, whether regime or regimen.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

PET and Requirements of the European and U.S. Pharmacopoeias

This test comprises artificially contaminating aliquots of formulation by means of a calibrated inoculum of specific microorganisms and incubating the same at precise temperatures. Samples are taken from the contaminated aliquots at given time intervals in order to count the microorganisms.

The European pharmacopoeia describes requirements which must be complied with during this test.

It makes it obligatory to test the following microorganisms:
Bacteria:
*Pseudomonas aeruginosa*, reference ATCC 9027; NCIMB 8626; CIP 82.118.
*Staphylococcus aureus*, reference ATCC 6538; NCTC 10788; NCIMB 9518; CIP 4.83.
Fungi:
*Candida albicans*, reference ATCC 10231; NCPF 3179; IP 48.72.
*Aspergillus niger*, reference ATCC 16404; IMI 149007; IP 1431.83. [34]

It also makes it obligatory to study the reductions in population of the microorganisms introduced into the formulation according to two acceptability criteria.

Since the A criteria are the most strict, it are less generally required that they be met.

In justified cases, when the A criteria cannot be complied with, for example owing to an increase in the risk of adverse reactions, the B criteria, which are less drastic, apply.

TABLE 2

European pharmacopoeia criteria:

| | Criteria | Logarithmic reduction at time required | | | |
|---|---|---|---|---|---|
| | | T48h | T7d | T14d | T28d |
| Bacteria | A | 2 | 3 | — | NI |
| | B | — | — | 3 | NI |
| Fungi | A | — | — | 2 | NI |
| | B | — | — | 1 | NI |

NI (Non-Increase) signifies that there must not be an increase in the number of microorganisms.

The U.S. pharmacopoeia itself also describes requirements which must be adhered to in order for the formulation to be protected. It also makes it obligatory to test the following microorganisms:
Bacteria:
*Escherichia coli*, reference ATCC 8739.
*Pseudomonas aeruginosa*, reference ATCC 9027.
*Staphylococcus aureus*, reference ATCC 6538.
Fungi:
*Candida albicans*, reference ATCC 10231.
*Aspergillus niger*, reference ATCC 16404.

It imposes logarithmic reductions in the population of microorganisms which are different than that of the European pharmacopoeia.

In the case of topical products, the conditions are:

TABLE 3

U.S. pharmacopoeia criteria:

| | Logarithmic reduction at time required | | | |
|---|---|---|---|---|
| | T48h | T7d | T14d | T28d |
| Bacteria | — | — | 2 | NI |
| Fungi | — | — | NI | NI |

Example 2

Study of the Antimicrobial Action of Ethanol Alone

This study is related to the "lotion" forms which are very common in dermatology. Ethanol is an excipient frequently used for this type of formulation.

The goal of this study is to determine the limiting proportion of ethanol which ensures antimicrobial preservation without the addition of preservatives. The effect of additional excipients was also evaluated with the aim of reducing the inhibitory ethanol concentration.

Search for the ethanol/water ratio which meets the criteria of the various pharmacopoeias in force.

J. J. Kabara in 1997 described that the proliferation of microorganisms can be prevented starting from 25% (v/v) of ethanol.

However, this extract does not describe the observed reductions in each microorganism studied in the PET. It is therefore impossible for us to confirm that the European and U.S. pharmacopoeia criteria are met at this concentration.

Simple ethanol/water mixtures were therefore studied in this sense.

The ethanol concentrations ranged from 5% to 30% in increments of 5%.

Results of Analyses:

TABLE 4

| | Log reduction observed | Criteria to be complied with | Met, not met | General conclusion |
|---|---|---|---|---|
| | 5% ethanol concentration: | | | |
| T2d | Sta: 0.2<br>Pseu: 0.4 | Eur. Criterion A<br>2 log reduction for the bacteria | Sta: Not met<br>Pseu: Not met | Does not meet European pharmacopoeia criteria A |
| T14d | Coli: 0.2<br>Sta: 5.8<br>Pseu: 0.9 | Eur. Criterion B<br>3 log reduction for the bacteria | Sta: Met<br>Pseu: Not met | Does not meet European pharmacopoeia criteria B |
| | | USP<br>2 log reduction for the bacteria | Coli: Not met<br>Sta: Met<br>Pseu: Not met | Does not meet USP criteria |

TABLE 5

| | Log reduction observed | Criteria to be complied with | Met, not met | General conclusion |
|---|---|---|---|---|
| | 10% ethanol concentration: | | | |
| T2d | Sta: 1<br>Pseu: 1.6 | Eur. Criterion A<br>2 log reduction for the bacteria | Sta: Not met<br>Pseu: Not met | Does not meet European pharmacopoeia criteria A. |
| T14d | Coli: 0.9<br>Sta: 5.8<br>Pseu: 6<br>Asp: 0.2 | Eur. Criterion B<br>3 log reduction for the bacteria<br>1 log reduction for the fungi | Sta: Met<br>Pseu: Met<br>Asp: Not met | Does not meet European pharmacopoeia criteria B |
| | | USP.<br>2 log reduction for the bacteria<br>no growth for the fungi | Coli: Not met<br>Sta: Met<br>Pseu: Met<br>Asp: Met | Does not meet USP criteria |

TABLE 6

| | Log reduction observed | Criteria to be complied with | Met, not met | General conclusion |
|---|---|---|---|---|
| | 15% ethanol concentration: | | | |
| T2d | Sta: 4<br>Pseu: 4 | Eur. Criterion A<br>2 log reduction for the bacteria | Sta: Met<br>Pseu: Met | Does not meet European pharmacopoeia criteria A |
| T14d | Coli: 6<br>Sta: 6<br>Pseu: 6<br>Can: 3.9<br>Asp: 0.6 | Eur. Criterion A<br>2 log reduction for the fungi<br>Eur. Criterion B<br>3 log reduction for the bacteria 1 log reduction for the fungi | Can: Met<br>Asp: Not met<br>Sta: Met<br>Pseu: Met<br>Can: Met<br>Asp: Not met | Does not meet European pharmacopoeia criteria B |
| | | USP.<br>2 log reduction for the bacteria no growth for the fungi | Coli: Met<br>Sta: Met<br>Pseu: Met<br>Asp: Met | Meets USP criteria |

TABLE 7

| | Log reduction observed | Criteria to be complied with | Met, not met | General conclusion |
|---|---|---|---|---|
| | 20% ethanol concentration: | | | |
| T2d | Sta: 4<br>Pseu: 4 | Eur. Criterion A<br>2 log reduction for the bacteria | Sta: Met<br>Pseu: Met | Does not meet European pharmacopoeia criteria A |
| T14d | Coli: 6<br>Sta: 6<br>Pseu: 6<br>Can: 3.9<br>Asp: 1.6 | Eur. Criterion A<br>2 log reduction for the fungi<br>Eur. Criterion B<br>3 log reduction for the bacteria<br>1 log reduction for the fungi | Can: Met<br>Asp: Not met<br>Sta: Met<br>Pseu: Met<br>Can: Met<br>Asp: Met | Meets European pharmacopoeia criteria B |
| | | USP<br>2 log reduction for the bacteria no growth for the fungi | Coli: Met<br>Sta: Met<br>Pseu: Met<br>Asp: Met | Meets USP criteria |

TABLE 8

| | Log reduction observed | Criteria to be complied with | Met, not met | General conclusion |
|---|---|---|---|---|
| | 25% ethanol concentration: | | | |
| T2d | Sta: 4<br>Pseu: 4 | Eur. Criterion A<br>2 log reduction for the bacteria | Sta: Met<br>Pseu: Met | Meets European pharmacopoeia criteria A |
| T14d | Coli: 6<br>Sta: 6<br>Pseu: 6<br>Can: 3.9<br>Asp: 3.8 | Eur. Criterion A<br>2 log reduction for the fungi<br>Eur. Criterion B<br>3 log reduction for the bacteria 1 log reduction for the fungi | Can: Met<br>Asp: Met<br>Sta: Met<br>Pseu: Met<br>Can: Met<br>Asp: Met | Meets European pharmacopoeia criteria B |
| | | USP<br>2 log reduction for the bacteria no growth for the fungi | Coli: Met<br>Sta: Met<br>Pseu: Met<br>Asp: Met | Meets USP criteria |

These results show that, starting from an ethanol concentration of 15% in the aqueous mixture, the bactericidal action thereof meets European pharmacopoeia criteria A and the USP criteria. However, this concentration is insufficient to completely inhibit the fungi. If the ethanol concentration is increased to 25%, the fungicidal action meets the requirements for all the pharmacopoeias. However, the concentration at which it exhibits a fungicidal activity is not readily compatible with good tolerance for topical application to the skin of a patient.

Example 2

Study of the Antimicrobial Action of Ethanol Coupled with Humectants

Tested was the mixture of ethanol with humectants in order to reduce the ethanol concentration in the composition and to evaluate the resulting antimicrobial protection provided thereby.

Three excipients used as humectants are frequently used for topical application. The action thereof makes it possible to maintain the water content in the stratum corneum. Propylene glycol (PG), glycerol and PEG 400 are compounds of this type. The impact of these excipients on the ethanol concentrations previously reported was studied.

Structural Formulae of the Humectants Used:

Propylene glycol

Glycerol

Polyethylene glycol

A limited number of combinations from the humectants and ethanol was studied.

At a given concentration of humectant, the lowest concentration of ethanol which meets the various criteria was sought.

Each of the three humectants was incorporated, at various concentrations ranging from 0% to 30% in increments of 5%, into solutions of ethanol, varying in the same proportions. Thus, 49 solutions were tested for each humectant.

Conclusion Regarding the Antimicrobial Actions of the Humectant/Ethanol Mixtures:

Propylene Glycol:

10% of PG enables the concentration of ethanol to be reduced from 25% to 15% so as to meet European pharmacopoeia criteria A.

30% by mass in an aqueous solution makes it possible to meet the USP criteria without the addition of ethanol.

Furthermore, at this concentration, the bacteria are inhibited while meeting European pharmacopoeia criteria A.

PG therefore has an action on all bacteria (gram+ and gram− combined).

It is, however, limited on fungi. In fact, alone, PG does not ensure a decrease in these microorganisms, in particular *Aspergillus niger*. It is therefore necessary to use ethanol in order to avoid proliferation of the latter.

Glycerol:

5% by mass of glycerol enables the ethanol concentration to be reduced from 25% to 15% so as to meet European pharmacopoeia criteria A.

The overall acceptability zone for the European pharmacopoeia criteria is similar to that obtained with PG.

10% by mass of glycerol enables the ethanol concentration to be reduced from 15% to 5% so as to meet the USP criteria.

However, the bactericidal action of glycerol is not as great as that of PG. Specifically, an aqueous solution containing 30% by mass of glycerol makes it possible to meet only European pharmacopoeia criteria B for bacteria, but does not meet the USP criteria. The elimination of fungi, in particular of *Aspergillus niger*, is still a blocking point which requires considerable provision of ethanol.

Polyethylene Glycol 400:

20% by mass of PEG 400 enables the ethanol concentration to be reduced from 25% to 10% so as to meet European pharmacopoeia criteria A.

20% by mass of PEG 400 enables the ethanol concentration to be reduced from 15% to 5% so as to meet the USP criteria.

The bactericidal action is not as great as that of PG, but is greater than that of glycerol.

The humectants tested made it possible to reduce the concentration of ethanol introduced into the aqueous solution.

According to the pharmacopoeias, the following "lotion"-type solutions are those which make it possible to provide antimicrobial protection without the addition of preservatives (Table No. 9).

TABLE 9

| | Solutions providing antimicrobial protection: | |
|---|---|---|
| | Pharma Europe | Pharma USP |
| Propylene glycol (PG) | starting from 15% EtOH starting from 5% PG | starting from 30% PG starting from 0% EtOH |
| Glycerol | starting from 15% EtOH starting from 5% glycerol | starting from 5% EtOH starting from 10% glycerol |
| Polyethylene glycol (PEG) | starting from 10% EtOH starting from 20% PEG | starting from 5% EtOH starting from 20% PEG |

The humectants studied promote the antimicrobial action of ethanol while at the same time making it possible to reduce the concentration thereof in the composition. However, their actions are not similar. It is possible to determine an order according to their bactericidal action.

PG>PEG 400>glycerol

Consequently, it will therefore be more advantageous to select PG or PEG as humectant owing to their properties on bacteria.

Example 3

Study of the Water Activity of the Compositions

The inhibitory action demonstrated with the addition of ethanol and of the three humectants can be interpreted as a direct bactericidal and fungicidal action.

However, these excipients also have the ability to modify the amount of free water available in the formulation. Their action can therefore be related to the water activity.

In addition, the viscosity of lotions for topical use can be potentially increased by the addition of a thickener (often hydrocolloids). The latter have, by definition, the particularity of trapping free water molecules present in a formulation. They therefore have the property of reducing the water activity, thereby influencing microbial proliferation.

The study comprises measuring the influence of the various compositions, lotions and gels and linking the water activity to the acceptability criteria of the various pharmacopoeias.

Water activity of glyco-ethanolic mixtures.

See the method of analysis in the appendix.

The humectants previously studied were also analyzed by means of the water activity.

Figure 1:
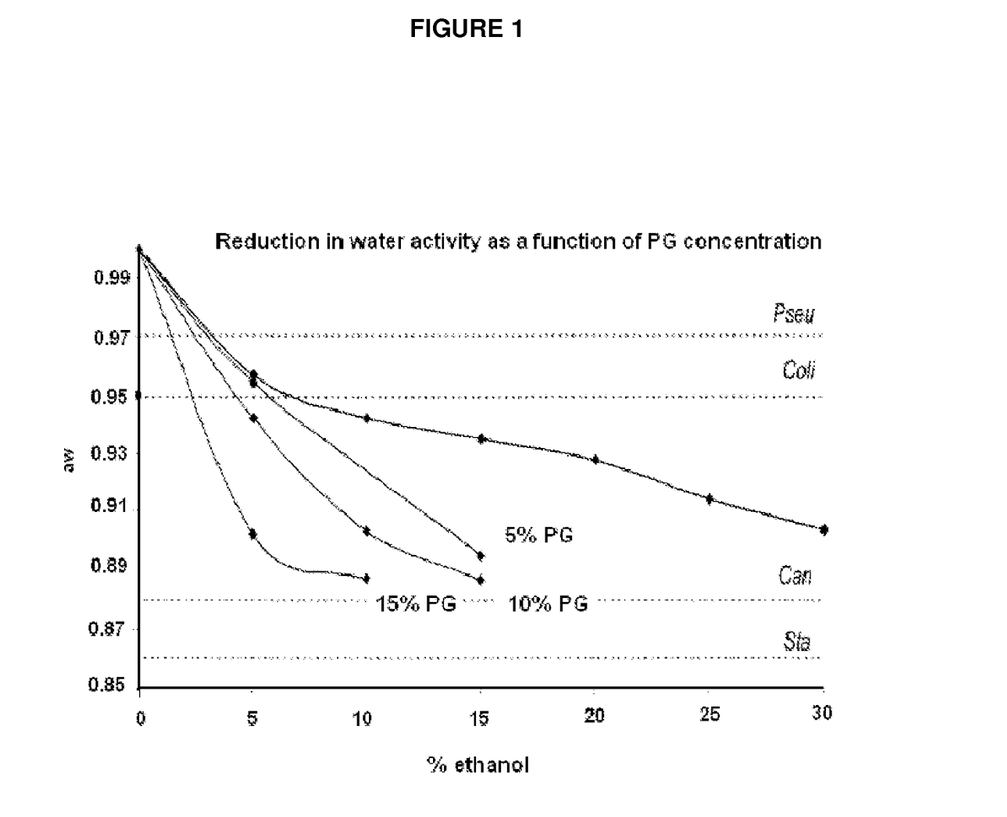
FIG. 1 is a graph showing reduction in water activity as a function of propylene glycol (PG) concentration.

Effect of Propylene Glycol (PG):

Figure No. 1: reduction in water activity as a function of PG concentration.

Figure 2:
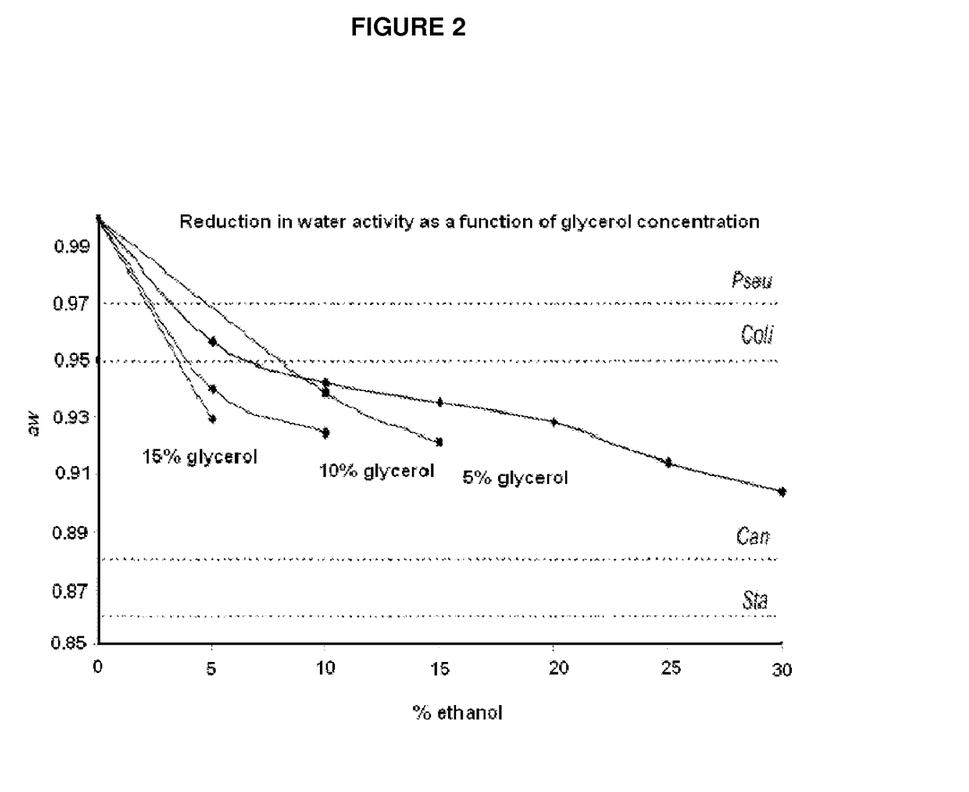
FIG. 2 is a graph showing reduction in water activity as a function of glycerol concentration.

Effect of Glycerol:

Figure No. 2: reduction in water activity as a function of glycerol concentration.

Figure 3:
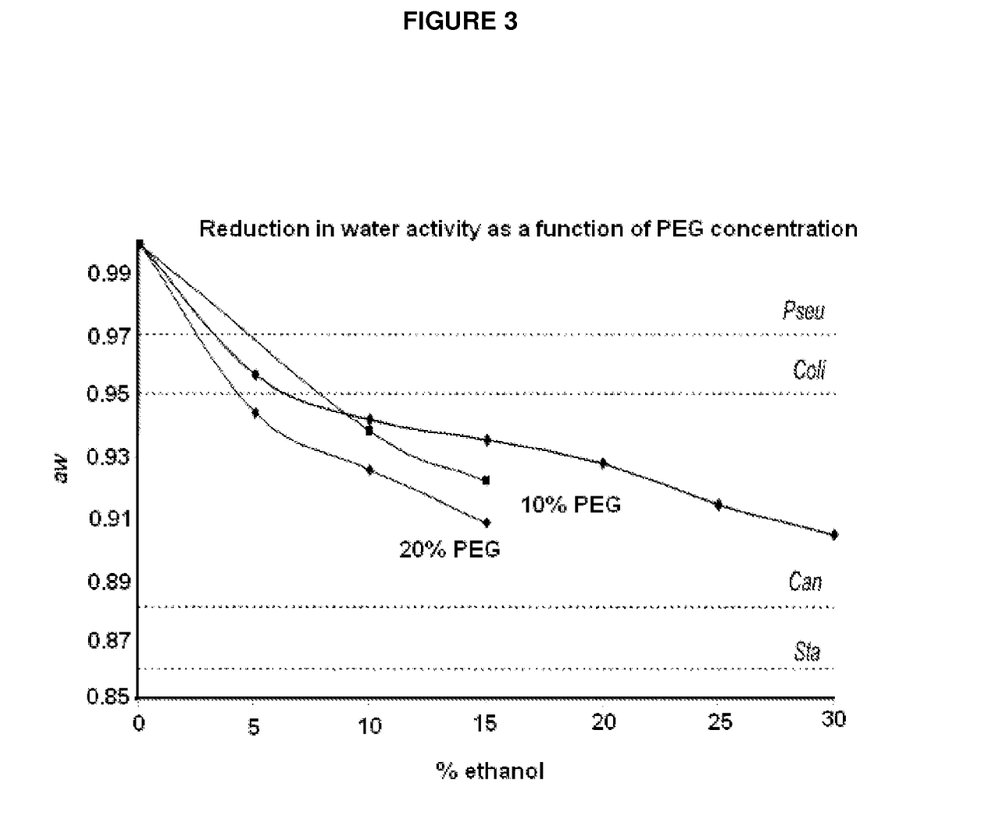
FIG. 3 is a graph showing reduction in water activity as a function of polyethylene glycol (PEG) concentration.

Effect of PEG 400:

Figure No. 3: reduction in water activity as a function of PEG concentration. At equal concentration, propylene glycol reduces the water activity to a greater extent than PEG 400, glycerol and than ethanol.

Example A

10% Humectant/10% Ethanol Mixtures $A_w$ PG=0.9036
$A_w$ glycerol: 0.9242
$A_w$ PG 400: 0.9380
PG>Glycerol>PEG.

Example B $A_w$ 30% PG=0.8906
$A_w$ 30% ethanol=0.9040
$A_w$ 30% glycerol=0.9070
PG>ethanol>glycerol.

It is therefore more advantageous to select PG owing to its greater action on water activity.

Example 4

Relationship from the Water Activity of the Formulations and Meeting the Pharmacopoeia Criteria TABLE No. 10

Relationship from the $a_w$ values and the PET action:

| Composition | | Aw | PET | Limiting value of $a_w$ for providing growth |
|---|---|---|---|---|
| | 5% EtOH | 0.9564 | Neither A nor B nor USP | $a_w$ = 0.97 Pseu $a_w$ = 0.95 Coli |
| 20% PEG 400 | 5% EtOH | 0.9442 | USP | |
| | 10% EtOH | 0.9422 | Neither A nor B nor USP | |
| 10% gly | 5% EtOH | 0.9400 | USP | |
| | 15% EtOH | 0.9382 | USP | |
| 5% gly | 10% EtOH | 0.9382 | USP | |
| 10% PEG 400 | 10% EtOH | 0.9380 | USP | |
| 15% gly | 5% EtOH | 0.9290 | USP | |
| | 20% EtOH | 0.9280 | USP, EP B | |
| 20% PEG 400 | 10% EtOH | 0.9258 | USP, EP A | |
| 10% gly | 10% EtOH | 0.9242 | USP | |
| 10% PEG 400 | 15% EtOH | 0.9218 | USP, EP A | |
| 5% gly | 15% EtOH | 0.9210 | USP, EP A | |
| | 25% EtOH | 0.9140 | USP, EP A | |
| 20% PEG 400 | 15% EtOH | 0.9082 | USP, EP A | |
| 30% gly | 0% EtOH | 0.9070 | Neither A nor B nor USP | |
| | 30% EtOH | 0.9040 | USP, EP A | |
| 10% PG | 10% EtOH | 0.9036 | USP | |
| 15% PG | 5% EtOH | 0.9026 | USP | |
| 5% PG | 15% EtOH | 0.8954 | USP, EP A | |
| 30% PG | 0% EtOH | 0.8906 | USP | |
| 15% PG | 10% EtOH | 0.8876 | USP | |
| 10% PG | 15% EtOH | 0.8868 | USP, EP A | $a_w$ = 0.88 Can |

Figure 4:
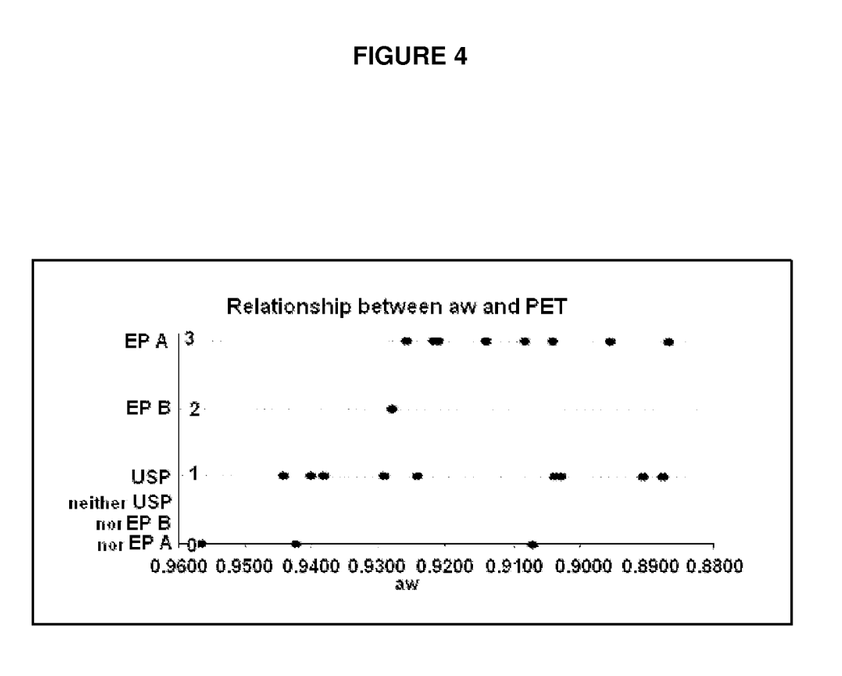
FIG. 4 is a graph showing a relationship between aw (water activity) and PET (Preservative Efficacy Test).

Figure No. 4: Search for a correlation from aw and the PET.

It may be noted that the results obtained with the PETs are not directly connected to the water activity of the formulations.

In fact, European pharmacopoeia criteria A, which are the most drastic, are not only met by formulations having a low $a_w$.

Furthermore, the $a_w$ values obtained are never lower than 0.8876. This content enables only the inhibition of Pseu and of Coll. Now, some formulations inhibit all the microorganisms while meeting European pharmacopoeia criteria A or the USP criteria.

It is not therefore the content of free water present in the formulations which provides the preservation, but indeed the antimicrobial action of the humectant/ethanol pairs.

Example 5

Study of the Effect of Thickeners in the Ethanolic Mixtures

The conventional thickeners for the formulator are:
Carbopol® (Ultrez 10 NF) at 0.5%,
Natrosol™ (HHX 250) at 1.5%, and
xanthan gum (Xantural 180) at 2%.

The thickeners studied do not all have the same gelling capacity. However, these gels analyzed should have a similar viscosity. For this reason, the concentrations of thickener introduced into the latter are different.

Effect on the Antimicrobial Properties

The action of these various gelling agents was first of all studied on water/ethanol mixtures having an alcohol concentration of 10% to 15%, which are the critical concentrations.

Natrosol™ is the thickener which makes it possible to reduce the ethanol concentration from 25% to 15%, meeting European pharmacopoeia criteria A.

All the thickeners tested make it possible to reduce the ethanol concentration from 15% to 10%, meeting the USP criteria.

Xanthan gum does not provide a good reduction of Sta. For this reason, 15% of ethanol coupled with xanthan gum meets only European pharmacopoeia criteria B.

Carbopol® and Natrosol™ coupled with 15% of ethanol reduces the bacteria, meeting European pharmacopoeia criteria A.

The major difference lies in the elimination of *Aspergillus niger*. Only ethanol Natrosol™ coupling provides elimination thereof (2.4 log reduction in 14 days) in accordance with European pharmacopoeia criteria A.

Their actions are not therefore similar. It is possible to determine an order of antimicrobial action.

Natrosol™>Carbopol®>xanthan gum

It is therefore more advantageous to select Natrosol™ coupled with 15% of ethanol owing to its action on *Aspergillus niger*.

The water activity of the various gels was measured.

The presence of each thickener resulted in the water activity being more or less reduced.

The greatest decrease is observed with Natrosol™ when it is introduced in 15% of ethanol.

Example 6

Study of the Effect of Thickeners in the Glyco-Ethanolic Mixtures

As demonstrated previously, thickeners have the ability to reduce the water activity and to therefore provide preservation at a lower ethanol content by shifting the acceptability zone.

Still from the viewpoint of reducing the amount of ethanol introduced into the solution, the accumulation of the action of humectants and of thickeners should be envisaged.

The thickener selected is Natrosol™ at 1.5% to the humectants selected are PG and PEG 400.

Propylene Glycol

Two formulations were analyzed:

1.5% Natrosol™, 30% PG: gel 1
1.5% Natrosol™, 10% ethanol, 15% PG: gel 2.

These formulations are tested in order to determine whether it is possible to completely eliminate the ethanol from the formulations (gel 1) and whether it is possible to shift the acceptability zone for European pharmacopoeia criteria A or B.

Without the gelling agent, these formulations passed neither the criteria A nor the criteria B of this pharmacopoeia.

The analysis carried out on gel 1 demonstrates that it does not meet European pharmacopoeia criteria A and B. Natrosol™ did not provide, for these concentrations, a variation in the acceptance zone for the European pharmacopoeia criteria.

For gel 2, the criteria A are met for all the microorganisms, with the exception of *Aspergillus niger*. The reduction observed for the latter is 1.2 log. Consequently, only the criteria B are met.

Natrosol™ provides a certain improvement with respect to acceptance for the criteria of this pharmacopoeia. The variation in $a_w$ has a direct consequence at certain concentrations since, gelled, the mixture of 10% ethanol and 15% PG passes European pharmacopoeia criteria B.

PEG 400

Two formulations were analyzed for the same reasons as previously.

1.5% Natrosol™, 30% PEG: gel 3
1.5% Natrosol™, 10% ethanol, 10% PEG: gel 4.

The action of PEG is not as great as that of PG under the same conditions. The PEG gels studied do not make it possible to vary the acceptability zone for the European pharmacopoeia and USP criteria.

Conclusion Regarding the Ethanolic Systems:

The combination of ethanol with glycols, in particular propylene glycol, is a valuable option since they have the ability to reduce the water activity. PG also has a considerable bactericidal action which makes it possible to reduce the alcohol concentration. The ratio from ethanol and the aqueous phase providing preservation drops to 15%.

The same ratio was determined by means of the study of the aqueous-ethanolic Natrosol™ gels.

Example of a Glyco-Ethanolic Mixture that can be Used in a Composition of Emulsion or Lotion Type:

15% ethanol, 5% PG and 3.5% glycerol.

This glycol combination made it possible to demonstrate their synergy since this emulsion more than passes European pharmacopoeia criteria A.

Example 7

Other Additives Having an Antimicrobial Efficacy

The goal of this study is to study families of molecules which could have an antimicrobial action by virtue of specific chemical functions.

Chelating agents and antioxidants will be analyzed in a standard formulation emulsion.

The emulsion selected is conventional, it being a typical formulation department emulsion.

The composition of the formulation is:

|  | Constituents | Percentage w/w |
|---|---|---|
| Fatty phase | Stearyl alcohol | 4.90 |
|  | EUMULGIN B2 PH | 2.10 |
|  | Cetyl alcohol | 1.50 |
|  | Liquid paraffin | 15.00 |
| Aqueous phase | Sterile water | Up to 100% |

This formulation will be the basis of all the following analyses. Thus, the molecules which will be tested will be introduced therein.

This formulation was analyzed using the preservative efficacy test (PET) in order to verify that this formulation contains no element which could inhibit microbial proliferation.

TABLE No. 11

Results of the analysis of the standard emulsion:

|  |  | Log reduction | | |
|---|---|---|---|---|
|  | Control | T48h | T7d | T14d |
| Coli | 6.0 | 0.1 | 0.1 | 0.1 |
| Sta | 6.0 | 0.2 | 0.3 | 1.7 |
| Pseu | 6.1 | 0 | −0.2 | −0.2 |
| Can | 6.0 | — | — | 0 |
| Asp | 6.0 | — | — | 0 |

It can clearly be seen that the emulsion selected has no antimicrobial action since no significant decrease in microorganisms is observed during the analysis times. This emulsion does not meet any criterion of any pharmacopoeia. The logarithmic reductions are very small or even nonexistent for all the microorganisms.

Thus, the possible decreases that it will be possible to observe over the course of the following analyses will indeed be due to the antimicrobial effects of the compounds tested.

The concentrations that were used are the upper limiting concentrations tolerated in the pharmaceutical field. Thus, if the criteria are not met, it will be unnecessary to retain the constituent as a potential microorganism inhibitor.

Chelating Agents, Disodium EDTA Dihydrate:

The EDTA was introduced into the aqueous phase at 0.15%. This concentration is the maximum concentration that can be used in the pharmaceutical field.

Antioxidants:

The antioxidants which are presented below are antioxidants commonly used in formulation.

Antioxidants Analyzed:

| | | |
|---|---|---|
| Natural antioxidants | Citric acid | 2% in the aqueous phase |
| | Sodium ascorbate | 2% in the aqueous phase |
| | Tocopherol | 0.05% in the emulsion prepared and cooled since the molecule is heat-sensitive |
| Synthetic antioxidants | BHT | 1% in the fatty phase |
| | Propyl gallate | 0.1% in the fatty phase |
| | Ascorbyl palmitate | 1% in the aqueous phase at 70° C. |

Results:

TABLE NO. 12

Analysis of the results obtained with each of the additives on each microorganism studied:

| | | Moulds | Yeast | Gram+ bacterium | Gram−bacterium | |
|---|---|---|---|---|---|---|
| Additives | % | Aspergillus Niger | Candida albicans | Staphylococcus aureus | Pseudomonas aeruginosa | Esoherichia coli |
| White emulsion | | − | − | − | − | − |
| EDTA | 0.15 | − | − | − | ++ | − |
| Citric acid | 2 | − | ++ | ++ | ++ | + |
| Sodium ascorbate | 2 | − | − | ++ | − | + |
| Tocopherol | 0.05 | − | − | − | − | − |
| BHT | 1 | − | − | − | − | − |
| Propyl gallate | 0.1 | − | − | − | ++ | − |
| Ascorbyl palmitate | 1 | − | − | ++ | ++ | + |
| Total | | − | ++ | ++ | ++ | + |

Legend:
− No European pharmacopoeia criterion or USP criterion is met
+ for the coli: the USP criteria are met
++ the European pharmacopoeia criteria A are met The study of the various actions of these additives reveals a great diversity in their behavior towards microorganisms.

It is possible to distinguish three quite distinct behaviors.

Tocopherol and BHT do not have a significant efficacy on the microorganisms as a whole. Their use will not therefore be retained for antimicrobial preservation.

EDTA and propyl gallate inhibit only *Pseudomonas aeruginosa*, meeting European pharmacopoeia criteria A.

Sodium ascorbate has a very good action on *Staphylococcus aureus*, meeting European pharmacopoeia criteria A, and *Escherichia coli*, meeting the USP criteria.

Citric acid and ascorbyl palmitate have a broader spectrum of efficacy. Specifically, both are bactericidal. The action of citric acid is greater since it inhibits, in addition to the bacteria, *Candida albicans* by virtue of a very low pH (pH=2.04).

Conclusion:

The results show that it is not possible to obtain a complete spectrum of action inhibiting all the microorganisms.

*Aspergillus niger* is the blocking element. None of the additives studied enabled even a minimal inhibition.

The elimination of moulds is the recurrent problem for each of the self-protecting approaches studied. Only ethanol at a high concentration made it possible to inhibit the development thereof.

It is therefore important to determine a preservative system which inhibits all the microorganisms, and in particular *Aspergillus niger*.

Example 8

Partial Use of a Conventional Preservative System

In order to ensure complete preservation of a matrix, it is important for the preservative system to inhibit bacteria and fungi.

Conventionally, a combination of antimicrobial preservatives, several parabens and phenoxyethanol, is used.

The concentrations of these preservatives are governed by regulations, the mixture of parabens should not exceed 0.8% of the formulation and the phenoxyethanol concentration is limited to 1%.

The entire conventional preservative system therefore is 1.8% of the mass of the formulation.

The previous study put forward numerous study approaches that may partially replace the preservative system. Thus, additives such as antioxidants or humectants which could provide the bactericidal action of the preservative system were put forward.

The use of preservative is therefore limited to the fungicidal action thereof.

For this, it was decided to select ascorbyl palmitate which provides the bactericidal action. Citric acid was not selected since the influence of the pH is a parameter that would constitute a much greater study. The results obtained would not be significant since two criteria are involved, the pH and the action of the molecule itself.

The fungicidal system can be obtained only with propylparaben, which has a greater action on these microorganisms than methylparaben and ethylparaben. Specifically, 250 ppm of propylparaben makes it possible to inhibit *Aspergillus niger* and *Candida albicans*, whereas 1000 ppm of methylparaben are necessary in order to obtain the same result. [9]

In order to reduce the provision of antimicrobial preservatives as much as possible, several concentrations of propylparaben were tested.

A concentration range of from 0.4% (maximum percentage authorized by the regulations) to 0.1%, in increments of 0.1%, was analyzed.

Compositions of the Emulsions Analyzed:

| No. | Constituents | % | % | % | % |
|---|---|---|---|---|---|
| Organic phase | Stearyl alcohol | 4.9 | 4.9 | 4.9 | 4.9 |
| | EUMULGIN B2 PH | 2.1 | 2.1 | 2.1 | 2.1 |
| | Cetyl alcohol | 1.5 | 1.5 | 1.5 | 1.5 |
| | Liquid paraffin | 15 | 15 | 15 | 15 |
| Aqueous phase | Sterile water | 75.1 | 75.2 | 75.3 | 75.4 |
| Antioxidant | Ascorbyl palmitate | 1 | 1 | 1 | 1 |
| Preservatives | Propylparaben | 0.4 | 0.3 | 0.2 | 0.1 |

Results of the PET:

TABLE No. 13

Results of the efficacy of the ascorbyl palmitate/propylparaben system:

| | Log reduction | | | |
|---|---|---|---|---|
| | Control | T48h | T7d | T14d |
| Emulsion containing 0.4% of propylparaben: | | | | |
| Coli | 5.9 | >3.9 | 4.8 | 5.9 |
| Sta | 5.9 | >3.9 | 4.2 | 4.8 |
| Pseu | 5.9 | >3.9 | 4.3 | 4.5 |
| Can | 5.9 | — | — | >4.0 |
| Asp | 5.9 | — | — | 3.3 |
| Emulsion containing 0.3% of propylparaben: | | | | |
| Coli | 5.9 | >3.9 | 4.5 | 5.9 |
| Sta | 5.9 | >3.9 | 4.7 | 4.7 |
| Pseu | 5.9 | >3.9 | 4.8 | 4.9 |
| Can | 5.9 | — | — | >4.0 |
| Asp | 5.9 | — | — | 3.0 |
| Emulsion containing 0.2% of propylparaben: | | | | |
| Coli | 5.9 | >3.9 | 5.9 | 5.9 |
| Sta | 5.9 | >3.9 | 4.8 | 5.9 |
| Pseu | 5.9 | >3.9 | 4.8 | 5.9 |
| Can | 5.9 | — | — | >4.0 |
| Asp | 5.9 | — | — | 2.0 |
| Emulsion containing 0.1% of propylparaben: | | | | |
| Coli | 5.9 | >3.9 | 3.7 | 4.6 |
| Sta | 5.9 | >3.9 | 3.7 | 4.2 |
| Pseu | 5.9 | >3.9 | 3.8 | 4.2 |
| Can | 5.9 | — | — | 4.8 |
| Asp | 5.9 | — | — | 2.0 |

All the formulations studied by means of the PET pass all the European pharmacopoeia and U.S. pharmacopoeia criteria. However, for the formulations containing 0.2% to 0.1% of propylparaben, the reduction in Asp observed is just equal to 2.0. For greater safety in the results, the formulation selected is that containing 0.3% of propylparaben and 1% of ascorbyl palmitate.

The percentage of antimicrobial preservative introduced into this emulsion is 0.3%, against 1.8% in conventional emulsions. The reduction in parabens and in preservatives was, as a general rule, therefore obtained through the use of 1% of ascorbyl palmitate.

Example 9

Combination of the Additives Studied in the Previous Examples

In order to completely eliminate the conventional preservative system from a composition, the following mixture is tested:

an antioxidant, ascorbyl palmitate at 1% by mass
a humectant, propylene glycol at 5% by mass
a percentage of water lower than previously, 50% by mass
an ethanol/aqueous phase ratio ranging from 10% to 15%.

Compositions of the Formulations Analyzed:

| No. | Constituents | % | % |
|---|---|---|---|
| Organic phase | Stearyl alcohol | 4.9 | 4.9 |
| | EUMULGIN B2 PH | 4 | 4 |
| | Cetyl alcohol | 1.5 | 1.5 |
| | Liquid paraffin | 39.6 | 39.6 |
| Aqueous phase | Sterile water | 38.13 | 39.9 |
| | Ethanol | 5.87 | 4.1 |
| | PG | 5 | 5 |
| Antioxidant | Ascorbyl palmitate | 1 | 1 |

Results of the PET:

TABLE No. 14

Results of emulsions No. 1 and No. 2:

| | Log reduction | | | |
|---|---|---|---|---|
| | Control | T48h | T7d | T14d |
| Emulsion No. 1 $R_{ethanol/aqueous\ phase} = 15$: | | | | |
| Coli | 5.9 | >3.9 | 5.9 | 5.9 |
| Sta | 5.9 | >3.9 | 5.9 | 5.9 |
| Pseu | 5.9 | >3.9 | 5.9 | 5.9 |
| Can | 5.9 | — | — | >4.0 |
| Asp | 5.9 | — | — | >3.9 |
| Emulsion No. 2 $R_{ethanol/aqueous\ phase} = 10$: | | | | |
| Coli | 5.9 | >3.9 | 5.9 | 5.9 |
| Sta | 5.9 | >3.9 | 5.9 | 5.9 |
| Pseu | 5.9 | >3.9 | 5.9 | 5.9 |
| Can | 5.9 | — | — | >4.0 |
| Asp | 5.9 | — | — | >3.9 |

All the criteria of the pharmacopoeias are more than met. This is because the reductions observed are very substantial. The log reduction in *Aspergillus niger* at time 14 days is greater than 3.9 for the two formulations. Emulsion No. 2, which contains the least amount of ethanol, can be selected since its action is as good as emulsion No. 1.

The water activity does not play a very important role here since, at this value, only the coli and the Pseu are inhibited.

The antimicrobial action observed is due to the synergistic effect of the combination of ascorbyl palmitate, ethanol and PG.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable pharmaceutical composition which comprises at least one pharmaceutically active agent and an effective antimicrobial amount of a preservative excipient mixture, wherein said preservative excipient mixture comprises ethanol, water, thickener, from 0.5% to 1% by mass of ascorbyl palmitate, 5% by mass of propylene glycol and an ethanol/aqueous phase ratio ranging from 10% to 15%, wherein the thickener is selected from the group consisting of an acrylic acid compound, a cellulosic compound, and xanthan gum.

2. The topically applicable pharmaceutical composition as defined by claim 1, formulated as an emulsion, cream, milk, ointment, impregnated pad, syndet, wipe, gel, spray, foam, lotion, stick, shampoo or washing base.

3. The topically applicable pharmaceutical composition as defined by claim 1, formulated as an aqueous emulsion or aqueous lotion.

4. The topically applicable pharmaceutical composition as defined by claim 1, wholly devoid of such known preservative(s).

5. The topically applicable pharmaceutical composition as defined by claim 1, said preservative excipient mixture further comprising a humectant, an antioxidant, a surfactant, and/or a chelating.

6. The topically applicable pharmaceutical composition as defined by claim 5, comprising a humectant selected from the group consisting of glycerol, glycerine, and polyethylene glycol.

7. The topically applicable pharmaceutical composition as defined by claim 5, comprising an antioxidant selected from the group consisting of an ascorbic acid compound, a citric acid compound, a tartaric acid compound, a lactate, a tocopherol, butylhydroxyanisole, butylhydroxytoluene, tertiary butylhydroquinone and propyl gallate.

8. The topically applicable pharmaceutical composition as defined by claim 5, comprising EDTA.

9. The topically applicable pharmaceutical composition as defined by claim 1, further comprising an antioxidant, a humectant, water and an ethanol/aqueous phase ratio ranging from 10% to 15%.

10. The topically applicable pharmaceutical composition as defined by claim 1, comprising less than 0.8% of a paraben.

11. The topically applicable pharmaceutical composition as defined by claim 10, comprising less than 0.4% of propyiparaben.

12. The topically applicable pharmaceutical composition as defined by claim 1, further comprising up to 1.8% by mass of at least one preservative selected from the group consisting of a formaldehyde-generating agent, a thiazine compound, a chlorinated compound, a phenolic compound, an alcoholic compound, bronopol, phenoxyethanol, a chloroxylenol, an acid compound, and/or benzalkonium chloride.

13. A composition of matter comprising a preservative excipient mixture, wherein the preservative excipient mixture comprises ethanol, water, thickener, from 0.5% to 1% by mass of ascorbyl palmitate, 5% by mass of propylene glycol and an ethanol laqueous phase ratio ranging from 10% to 15% wherein the thickener is selected from the group consisting of an acrylic acid compound, a cellulosic compound, and xanthan gum.

14. The composition as defined in claim 13, wherein the composition further comprises up to 1.8% by mass of at least one preservative selected from the group consisting of a formaldehyde-generating agent, a thiazine compound, a chlorinated compound, a phenolic compound, an alcoholic compound, bronopol, phenoxvethanol, a chloroxylenol an acid compound, and/or benzalkonium chloride.

15. The topically applicable pharmaceutical composition as defined by claim 12, wherein the formaldehyde-generating agent is imidazolidinylurea or diazolidinylurea.

16. The topically applicable pharmaceutical composition as defined by claim 12, wherein the thiazine compound is methylchloroisothiazolinone (MCI).

17. The topically applicable pharmaceutical composition as defined by claim 12, wherein the chlorinated compound is chlorhexidine.

18. The topically applicable pharmaceutical composition as defined by claim 12, wherein the phenolic compound is paraben.

19. The topically applicable pharmaceutical composition as defined by claim 12, wherein the acid compound is sorbic acid or benzoic acid.

20. A topically applicable pharmaceutical composition which comprises at least one pharmaceutically active agent and an effective antimicrobial amount of a preservative excipient mixture, wherein said preservative excipient mixture comprises ethanol, water, EDTA, from 0.5% to 1% by mass of ascorbyl palmitate, 5% by mass of propylene glycol and an ethanol aqueous phase ratio ranging from 10% to 15%.

* * * * *